US011679028B2

(12) United States Patent
Quintana et al.

(10) Patent No.: US 11,679,028 B2
(45) Date of Patent: Jun. 20, 2023

(54) MULTI-DOSE OCULAR FLUID DELIVERY SYSTEM

(71) Applicant: NOVARTIS AG, Basel (CH)

(72) Inventors: Reynaldo Quintana, Menlo Park, CA (US); Yehuda Ivri, Newport Coast, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/811,879

(22) Filed: Mar. 6, 2020

(65) Prior Publication Data

US 2020/0281768 A1 Sep. 10, 2020

Related U.S. Application Data

(60) Provisional application No. 62/951,903, filed on Dec. 20, 2019, provisional application No. 62/814,773, filed on Mar. 6, 2019.

(51) Int. Cl.
*A61F 9/00* (2006.01)
(52) U.S. Cl.
CPC .................................. *A61F 9/0026* (2013.01)
(58) Field of Classification Search
CPC ..... A61F 9/0026; A61F 9/0008; A45D 34/00; A61M 11/005; A61M 15/0028; B05B 11/007; B05B 11/3032; B05B 17/04; B05B 17/0607; B05B 17/0623; B05B 17/0646
See application file for complete search history.

(56) References Cited

U.S. PATENT DOCUMENTS

| 3,640,274 A | 2/1972 | Costello |
| 3,779,245 A | 12/1973 | Windsor |
| 3,812,854 A | 5/1974 | Buckles |
| 3,861,386 A | 1/1975 | Harris |

(Continued)

FOREIGN PATENT DOCUMENTS

| CN | 103118642 A | 5/2013 |
| CN | 104146816 A | 11/2014 |

(Continued)

OTHER PUBLICATIONS

Birkhoff et al., "Advanced delivery devices", 2010, Drug Delivery Technology Nov./Dec. 2010 vol. 10 No. 9, 16-21.

(Continued)

*Primary Examiner* — Jessica Arble
*Assistant Examiner* — Alessandro R Del Priore
(74) *Attorney, Agent, or Firm* — Greenberg Traurig, LLP; Chinh H. Pham; Joshua I. Rudawitz (57) ABSTRACT

Multi-dose ocular fluid delivery devices are provided. Aspects of the fluid delivery devices include a fluid package and an actuator. The fluid package includes a reservoir of an ophthalmic formulation, an aperture and a valve member for sealing the aperture when fluid is not being ejected therethrough. The actuator is configured to operate the valve member so as to at least reduce, if not prevent, ingress of outside materials or contaminants into the reservoir, such that the ophthalmic formulation present in the reservoir does not require a preservative (e.g., where a preservative-free ophthalmic formulation is present in the reservoir). Also provided are methods of using the devices in fluid delivery applications, as well as a kit that includes components of the devices.

13 Claims, 5 Drawing Sheets

(56) References Cited

U.S. PATENT DOCUMENTS

| | | | |
|---|---|---|---|
| 3,970,250 | A * | 7/1976 | Drews .................. A61M 11/005 239/102.2 |
| 3,976,072 | A | 8/1976 | Walker |
| 4,159,803 | A | 7/1979 | Cameto |
| 4,300,546 | A | 11/1981 | Kruber |
| 4,334,531 | A | 6/1982 | Reichl |
| 4,338,576 | A | 7/1982 | Takahashi |
| 4,352,459 | A | 10/1982 | Berger |
| 4,465,234 | A | 8/1984 | Maehara |
| 4,632,311 | A | 12/1986 | Nakane |
| 4,655,393 | A | 4/1987 | Berger |
| 4,850,534 | A | 7/1989 | Takahashi |
| 4,882,150 | A | 11/1989 | Kaufman |
| 4,952,581 | A | 8/1990 | Bito |
| 4,961,345 | A | 10/1990 | Tsuruoka |
| 4,976,259 | A | 12/1990 | Higson |
| 4,981,625 | A | 1/1991 | Rhim |
| 5,025,957 | A * | 6/1991 | Ranalletta ............. B05B 11/047 222/189.09 |
| 5,171,306 | A | 12/1992 | Vo |
| 5,232,363 | A | 8/1993 | Meller |
| 5,368,582 | A | 11/1994 | Bertera |
| 5,370,317 | A | 12/1994 | Weston |
| 5,487,378 | A | 1/1996 | Robertson |
| 5,549,249 | A * | 8/1996 | Foster .................. B05B 1/3431 239/463 |
| 5,624,057 | A | 4/1997 | Lifshey |
| 5,627,611 | A | 5/1997 | Scheiner |
| 5,630,793 | A | 5/1997 | Rowe |
| 5,657,926 | A | 8/1997 | Toda |
| 5,692,651 | A | 12/1997 | Fuchs |
| 5,811,443 | A | 9/1998 | DeSantis, Jr. |
| 5,938,117 | A | 8/1999 | Ivri |
| 5,958,342 | A | 9/1999 | Gamble |
| 6,024,717 | A | 2/2000 | Ball |
| 6,062,212 | A | 5/2000 | Davison |
| 6,065,623 | A | 5/2000 | Hierzer |
| 6,095,376 | A | 8/2000 | Hennemann |
| 6,232,129 | B1 | 5/2001 | Wiktor |
| 6,273,092 | B1 | 8/2001 | Nolan |
| 6,302,101 | B1 | 10/2001 | Py |
| 6,467,476 | B1 | 10/2002 | Ivri |
| RE38,077 | E | 4/2003 | Cohen |
| 6,543,442 | B2 | 4/2003 | Gonda |
| 6,629,646 | B1 | 10/2003 | Ivri |
| 6,730,066 | B1 | 5/2004 | Bennwik |
| 6,758,837 | B2 | 7/2004 | Peclat |
| 7,066,398 | B2 | 6/2006 | Borland |
| 7,105,357 | B1 | 9/2006 | Kalkum |
| 7,201,732 | B2 | 4/2007 | Anderson |
| 7,314,938 | B2 | 1/2008 | Shen |
| 7,571,722 | B2 | 8/2009 | Wuttke |
| 7,745,460 | B2 | 6/2010 | Shen |
| 7,790,743 | B2 | 9/2010 | Shen |
| 7,874,467 | B2 | 1/2011 | Pardes |
| 7,883,031 | B2 | 2/2011 | Collins, Jr. |
| 7,928,122 | B2 | 4/2011 | Shen |
| 8,012,136 | B2 | 9/2011 | Collins, Jr. |
| 8,048,047 | B2 | 11/2011 | Domash |
| 8,056,766 | B2 | 11/2011 | Grevin |
| 8,128,606 | B2 | 3/2012 | Anderson |
| 8,133,210 | B2 | 3/2012 | Al-Abdulla |
| 8,144,399 | B2 | 3/2012 | Steenblik |
| 8,168,655 | B2 | 5/2012 | Gadek |
| 8,273,307 | B2 | 9/2012 | Eickhoff |
| 8,367,701 | B2 | 2/2013 | Burnier |
| 8,398,001 | B2 | 3/2013 | Borland |
| 8,435,544 | B2 | 5/2013 | Mitra |
| 8,544,462 | B2 | 10/2013 | Papania |
| 8,545,463 | B2 | 10/2013 | Collins, Jr. |
| 8,592,450 | B2 | 11/2013 | Gadek |
| 8,629,111 | B2 | 1/2014 | Acheampong |
| 8,633,162 | B2 | 1/2014 | Acheampong |
| 8,642,556 | B2 | 2/2014 | Acheampong |
| 8,648,048 | B2 | 2/2014 | Acheampong |
| 8,684,980 | B2 | 4/2014 | Hunter |
| 8,685,930 | B2 | 4/2014 | Acheampong |
| 8,722,728 | B2 | 5/2014 | Wong |
| 8,733,935 | B2 | 5/2014 | Ballou, Jr. |
| 8,863,998 | B2 | 10/2014 | Painchaud |
| 8,927,574 | B2 | 1/2015 | Burnier |
| 8,927,921 | B1 | 1/2015 | Nelms |
| 8,936,021 | B2 | 1/2015 | Collins, Jr. |
| 9,039,666 | B2 | 5/2015 | Voss |
| 9,068,566 | B2 | 6/2015 | Ivri |
| 9,085,553 | B2 | 7/2015 | Zeller |
| 9,087,145 | B2 | 7/2015 | Ballou, Jr. |
| 9,186,690 | B2 | 11/2015 | Scanlon |
| 9,216,174 | B2 | 12/2015 | Shen |
| 9,238,532 | B2 | 1/2016 | Decock |
| 9,248,191 | B2 | 2/2016 | Acheampong |
| 9,353,088 | B2 | 5/2016 | Burnier |
| 9,447,077 | B2 | 9/2016 | Burnier |
| 9,597,230 | B2 | 3/2017 | Haffner |
| 9,676,525 | B2 | 6/2017 | Greiner-Perth |
| 9,700,686 | B2 | 7/2017 | Gavini |
| 9,801,757 | B2 | 10/2017 | Voss |
| 9,808,825 | B2 | 11/2017 | Aguilar |
| 9,867,933 | B2 | 1/2018 | Pardes |
| 9,890,141 | B2 | 2/2018 | Burnier |
| 10,073,949 | B2 | 9/2018 | Ballou, Jr. |
| 10,105,720 | B2 | 10/2018 | Decock |
| 10,124,000 | B2 | 11/2018 | Shen |
| 10,154,923 | B2 | 12/2018 | Hunter |
| 10,174,017 | B2 | 1/2019 | deLong |
| 10,314,740 | B2 | 6/2019 | Kraft |
| 10,624,781 | B2 | 4/2020 | Ivri |
| 11,278,448 | B2 | 3/2022 | Palanker |
| 2001/0036424 | A1 | 11/2001 | Takahashi |
| 2001/0036449 | A1 | 11/2001 | Garst |
| 2002/0078947 | A1 | 6/2002 | Gumaste |
| 2002/0124843 | A1 | 9/2002 | Skiba |
| 2002/0158196 | A1 | 10/2002 | Berggren |
| 2002/0161344 | A1 | 10/2002 | Peclat |
| 2002/0185125 | A1 | 12/2002 | Klimowicz |
| 2003/0052573 | A1 | 3/2003 | Wischnewskiy |
| 2003/0065294 | A1 | 4/2003 | Pickup |
| 2003/0071071 | A1 | 4/2003 | Garcia |
| 2003/0140921 | A1 | 7/2003 | Smith |
| 2004/0039355 | A1 | 2/2004 | Gonzalez |
| 2004/0050861 | A1 | 3/2004 | Lisec |
| 2004/0138630 | A1 | 7/2004 | Al-Abdulla |
| 2004/0163645 | A1 | 8/2004 | Connelly |
| 2004/0173642 | A1 | 9/2004 | Clifford |
| 2004/0204674 | A1 | 10/2004 | Anderson |
| 2004/0215157 | A1 | 10/2004 | Peclat |
| 2004/0256487 | A1 | 12/2004 | Collins |
| 2005/0001981 | A1 | 1/2005 | Anderson |
| 2005/0006417 | A1 | 1/2005 | Nicol |
| 2005/0107832 | A1 | 5/2005 | Bemabei |
| 2005/0172962 | A1 | 8/2005 | Gumaste |
| 2005/0240162 | A1 | 10/2005 | Chen |
| 2005/0261641 | A1 | 11/2005 | Warchol |
| 2006/0065677 | A1 * | 3/2006 | Py ...................... A61M 35/003 222/383.1 |
| 2006/0069358 | A1 | 3/2006 | Gerondale |
| 2006/0147313 | A1 | 7/2006 | Zengerle |
| 2007/0051362 | A1 | 3/2007 | Sullivan |
| 2007/0088267 | A1 | 4/2007 | Shekalim |
| 2007/0088268 | A1 | 4/2007 | Edwards |
| 2007/0102455 | A1 | 5/2007 | Stark |
| 2007/0119969 | A1 | 5/2007 | Collins |
| 2007/0195151 | A1 | 8/2007 | Anderson |
| 2007/0268340 | A1 | 11/2007 | Dacquay |
| 2008/0039807 | A1 | 2/2008 | Pine |
| 2008/0202514 | A1 | 8/2008 | Kriksunov |
| 2008/0214940 | A1 | 9/2008 | Benaron |
| 2008/0233053 | A1 | 9/2008 | Gross |
| 2008/0247264 | A1 | 10/2008 | Gabi |
| 2008/0257911 | A1 | 10/2008 | Choi |
| 2009/0060793 | A1 | 3/2009 | Eickhoff |
| 2009/0114742 | A1 | 5/2009 | Collins, Jr. |
| 2009/0134235 | A1 | 5/2009 | Ivri |
| 2009/0182291 | A1 | 7/2009 | Eilat |

(56) References Cited

U.S. PATENT DOCUMENTS

| | | |
|---|---|---|
| 2009/0192443 A1 | 7/2009 | Collins, Jr. |
| 2009/0212127 A1 | 8/2009 | Reynolds |
| 2009/0212133 A1 | 8/2009 | Collins, Jr. |
| 2009/0223513 A1 | 9/2009 | Papania |
| 2010/0001090 A1 | 1/2010 | Neergaard |
| 2010/0005903 A1 | 1/2010 | Beavis |
| 2010/0013352 A1 | 1/2010 | Pletner |
| 2010/0044460 A1 | 2/2010 | Sauzade |
| 2010/0072301 A1 | 3/2010 | Cater |
| 2010/0072302 A1* | 3/2010 | Cater .............. B05B 1/3053 239/333 |
| 2010/0076388 A1 | 3/2010 | Cater |
| 2010/0147899 A1 | 6/2010 | Nardi |
| 2010/0222752 A1 | 9/2010 | Collins, Jr. |
| 2010/0236545 A1 | 9/2010 | Kem |
| 2010/0295420 A1 | 11/2010 | Wierach |
| 2011/0074247 A1 | 3/2011 | Hohlfeld |
| 2011/0102735 A1 | 5/2011 | Gupta |
| 2011/0106025 A1 | 5/2011 | Hall |
| 2011/0284579 A1 | 11/2011 | Pardes |
| 2011/0293452 A1 | 12/2011 | Kim |
| 2012/0017898 A1 | 1/2012 | Moller |
| 2012/0062840 A1 | 3/2012 | Ballou, Jr. |
| 2012/0070467 A1* | 3/2012 | Ballou, Jr. .............. G16H 30/20 424/400 |
| 2012/0143152 A1* | 6/2012 | Hunter .............. A61B 5/0059 604/298 |
| 2012/0179122 A1 | 7/2012 | Eilat |
| 2012/0197219 A1 | 8/2012 | Scanlon |
| 2012/0304929 A1 | 12/2012 | Ivri |
| 2013/0002095 A1 | 1/2013 | Van der Linden |
| 2013/0017283 A1 | 1/2013 | Zemel |
| 2013/0025038 A1 | 1/2013 | Frey |
| 2013/0053042 A1 | 2/2013 | Tanikawa |
| 2013/0118619 A1 | 5/2013 | Loth |
| 2013/0140225 A1 | 6/2013 | Decock |
| 2013/0150812 A1 | 6/2013 | Hunter |
| 2013/0152796 A1 | 6/2013 | Pawl |
| 2013/0153677 A1 | 6/2013 | Leen |
| 2013/0172830 A1 | 7/2013 | Hunter |
| 2013/0206857 A1 | 8/2013 | Ivri |
| 2013/0299607 A1 | 11/2013 | Wilkerson |
| 2013/0345672 A1 | 12/2013 | Ferreri |
| 2014/0088524 A1 | 3/2014 | Marx |
| 2014/0113946 A1 | 4/2014 | Abad |
| 2014/0157956 A1 | 6/2014 | Date |
| 2014/0171490 A1 | 6/2014 | Gross |
| 2014/0187969 A1 | 7/2014 | Hunter |
| 2014/0214024 A1 | 7/2014 | Eichler |
| 2014/0224267 A1 | 8/2014 | Levitz |
| 2014/0242022 A1 | 8/2014 | Vehige |
| 2014/0249491 A1 | 9/2014 | Ballou, Jr. |
| 2014/0257172 A1 | 9/2014 | Yalamanchili |
| 2014/0274910 A1 | 9/2014 | Cumberlidge |
| 2014/0276054 A1 | 9/2014 | Hossack |
| 2014/0285121 A1 | 9/2014 | Balogh |
| 2014/0323931 A1 | 10/2014 | Avni |
| 2014/0336596 A1 | 11/2014 | Wochele |
| 2014/0336618 A1 | 11/2014 | Wilkerson |
| 2015/0018781 A1 | 1/2015 | Rinderknect |
| 2015/0035180 A1 | 2/2015 | Shen |
| 2015/0036219 A1 | 2/2015 | Shen |
| 2015/0040891 A1 | 2/2015 | Avni |
| 2015/0086397 A1 | 3/2015 | Ma |
| 2015/0097050 A1 | 4/2015 | Ciervo |
| 2015/0139973 A1 | 5/2015 | Steinfeld |
| 2015/0144128 A1 | 5/2015 | Hijlkema |
| 2015/0209174 A1 | 7/2015 | Abreu |
| 2015/0209178 A1* | 7/2015 | Blakey .............. A61F 9/0008 604/290 |
| 2015/0238689 A1 | 8/2015 | Shimizu |
| 2015/0256730 A1 | 9/2015 | Shen |
| 2015/0276994 A1 | 10/2015 | Shen |
| 2015/0308421 A1 | 10/2015 | Vogt |
| 2015/0328151 A1 | 11/2015 | Ballou, Jr. |
| 2015/0352297 A1* | 12/2015 | Stedman .............. A61M 15/0036 128/200.14 |
| 2016/0107180 A1 | 4/2016 | Decock |
| 2016/0120833 A1 | 5/2016 | Wan |
| 2016/0129467 A1* | 5/2016 | Ciardella .............. B05B 1/02 222/1 |
| 2016/0199225 A1 | 7/2016 | Ivri |
| 2016/0199230 A1 | 7/2016 | Doshi |
| 2016/0213866 A1* | 7/2016 | Tan .............. A61M 11/005 |
| 2016/0263314 A1* | 9/2016 | Pardes .............. B05B 11/007 |
| 2016/0296367 A1 | 10/2016 | Ivri |
| 2016/0354559 A1 | 12/2016 | Gavini |
| 2017/0028626 A1 | 2/2017 | Delrot |
| 2017/0136484 A1 | 5/2017 | Wilkerson |
| 2017/0151088 A1 | 6/2017 | Ballou, Jr. |
| 2017/0156927 A1 | 6/2017 | Richter |
| 2017/0182510 A1 | 6/2017 | Wilkerson |
| 2017/0187969 A1 | 6/2017 | Kitamori |
| 2017/0274159 A1 | 9/2017 | Gavini |
| 2017/0344714 A1 | 11/2017 | Ballou, Jr. |
| 2018/0085251 A1 | 3/2018 | Hunter |
| 2018/0108275 A1 | 4/2018 | Newberry |
| 2018/0116871 A1 | 5/2018 | Hunter |
| 2018/0207030 A1 | 7/2018 | Ivri |
| 2018/0229247 A1* | 8/2018 | Laidler .............. B05B 1/3405 |
| 2018/0297053 A1 | 10/2018 | Buckland |
| 2019/0053945 A1 | 2/2019 | Hunter |
| 2019/0074086 A1 | 3/2019 | Ballou, Jr. |
| 2019/0099071 A1 | 4/2019 | Ehrmann |
| 2019/0314195 A1 | 10/2019 | Ivri |
| 2019/0314196 A1 | 10/2019 | Ivri |
| 2019/0314197 A1 | 10/2019 | Ivri |
| 2019/0314198 A1 | 10/2019 | Ivri |
| 2020/0022416 A1 | 1/2020 | Alarcon |
| 2020/0197218 A1 | 6/2020 | Newell |
| 2020/0246182 A1 | 8/2020 | Ivri |
| 2020/0281768 A1 | 9/2020 | Quintana |
| 2020/0315842 A1 | 10/2020 | Palanker |
| 2020/0330267 A1 | 10/2020 | Li |
| 2021/0128350 A1 | 5/2021 | Ivri |
| 2021/0137732 A1 | 5/2021 | Quintana |
| 2021/0220169 A1 | 7/2021 | Ivri |
| 2021/0322209 A1 | 10/2021 | Ivri |
| 2021/0322210 A1 | 10/2021 | Ivri |
| 2022/0039998 A1 | 2/2022 | Ivri |
| 2022/0125631 A1 | 4/2022 | Ianchulev |
| 2022/0160542 A1 | 5/2022 | Palanker |
| 2022/0192874 A1 | 6/2022 | Ivri |

FOREIGN PATENT DOCUMENTS

| | | | |
|---|---|---|---|
| CN | 104582647 A | 4/2015 | |
| CN | 204813955 U | 12/2015 | |
| CN | 107530509 A | 1/2018 | |
| EP | 0622035 B1 | 3/1999 | |
| EP | 1493410 A2 | 1/2005 | |
| JP | 3055480 U | 1/1999 | |
| JP | 2007531577 A | 11/2007 | |
| JP | 2013535250 A | 9/2013 | |
| WO | 1994020875 A3 | 1/1995 | |
| WO | 1996000050 A1 | 1/1996 | |
| WO | WO-9600050 A1 * | 1/1996 | .......... A61F 9/0008 |
| WO | 2001046134 A1 | 6/2001 | |
| WO | 2002072169 A2 | 9/2002 | |
| WO | WO2010/078428 | 7/2010 | |
| WO | 2012009706 A1 | 1/2012 | |
| WO | 2013076682 A1 | 5/2013 | |
| WO | WO-2013076682 A1 * | 5/2013 | .......... A61M 11/007 |
| WO | 2013090459 A1 | 6/2013 | |
| WO | 2013090468 A1 | 6/2013 | |
| WO | 2013155201 A2 | 10/2013 | |
| WO | 2013158967 A3 | 12/2013 | |
| WO | 2016115050 A1 | 7/2016 | |
| WO | 2016164830 A1 | 10/2016 | |
| WO | 2018136618 A2 | 7/2018 | |
| WO | WO-2018136618 A2 * | 7/2018 | .......... A61F 9/0008 |
| WO | WO2018/227190 | 12/2018 | |

(56) References Cited

FOREIGN PATENT DOCUMENTS

| WO | 2019113483 A1 | 6/2019 |
|---|---|---|
| WO | WO2020/010116 | 1/2020 |

OTHER PUBLICATIONS

International Search Report and Written Opinion dated Jun. 5, 2020 in corresponding International Patent Application No. PCT/US2020/021504 (7 pages).
International Search Report and Written Opinion dated Mar. 29, 2021 in corresponding International Patent Application No. PCT/US2020/066169 (7 pages).
Abidi et al., "Lifilegrast: A Novel Drug for Treatment of Dry Eye Disease", Journal of Pharmacology and Pharmacotherapy, 2016, vol. 7, pp. 194-198.
Ali et al., "Glaucoma and Dry Eye", Ophthalmology, 2009, vol. 116, p. 1232.
Brenton, "CRUK/10/30: TRICON8—Sample collection of ovarian cancer tissues and blood for translational research from patients participating in the CR-UK/MRC ICON8 trial", 2015, online abstract.
Choi et al., "Generation of Controllable Monodispersed Sprays Using Impulse Jet and Charging Techniques", Review of Scientific Instruments, 1990, vol. 61, pp. 1689-1693.
Denion et al., "A 5-Minute Interval between Two Dilating Eye Drops Increases Their Effect", Jul. 19, 2017, Optometry and Vision Science, vol. 94, pp. 838-844.
Electronic Tutorials, "Linear Solenoid Actuator", 2016 [online]; [Retrieved on Oct. 17, 2022], Retrieved from the Internet [URL: https://www.electronics-tutorials.ws/io/io_6.html].
Elert, Glenn, "Spherical mirrors", The Physics Hypertextbook, 2021 [online]; [Retrieved on Oct. 17, 2022], Retrieved from the Internet [URL: https://physics.info/mirrors/].
Gannon, Megan, "The Best Length for Eyelashes, According to Science", Feb. 24, 2015 [online]; [Retrieved on Oct. 17, 2022], Retrieved from the Internet [URL: https://www.livescience.com/49934-optimal-length-for-eyelashes-discovered.html ].
Ianchulev et al., "Pharmacodynamic profile of mydriatic agents delivered by ocular piezo-ejection microdosing compared with conventional eyedropper", 2016, Ther. Deliv., vol. 7, pp. 751-760.
Jow et al., "Design and Optimization of Printed Spiral Coils for Efficient Transcutaneous Inductive Power Transmission", IEEE Transactions on Biomedical Circuits and Systems, 2007, vol. 1, pp. 193-202.
Kent, Christopher, "Getting Meds onto the Eye, 21st Century Style", Mar. 15, 2013 [online]; [Retrieved on Aug. 27, 2019], Retrieved from the Internet [URL: https://www.reviewofophthalmology.com/article/getting-meds-onto-the-eye-21st-century-style].
Kompella et al., "ISOPT Clinical Hot Topic Panel Discussion on Ocular Drug Delivery", 2019, J. Ocul. Pharmacol. Ther., vol. 35, pp. 457-465.
Lallemand et al., "Cyclosporine A Delivery to the Eye: A Comprehensive Review of Academic and Industrial Efforts", European Journal of Pharmaceutics and Biopharmaceutics, 2017, vol. 117, pp. 14-28.
Lindblad et al., "Production of Uniform-Sized Liquid Droplets", Journal of Scientific Instruments, 1965, vol. 42, pp. 635-638.
Lux et al., "A Comparative Bioavailability Study of Three Conventional Eye Drops Versus a Single Lyophilisate", Br. J. Ophthalmol., 2003, vol. 87, pp. 436-440.
Macmillan Online Dictionary, "Stream," n.d. [online]; [Retrieved on Dec. 13, 2018]; Retrieved from the Internet [URL: https://macmillandictionary.com/dictionary/american/stream_1#stream_9].
Marx et al., "Opthalmic Squeeze Dispenser: Eliminating the Need for Additives in Multidose Preservative-Free Eyecare Formulations", 2017, Drug Development Delivery, vol. 17, pp. 40-44.
Merriam-Webster, "Clamp," 2019 [online]; [Retrieved on Oct. 25, 2022], Retrieved from the Internet [URL: https://www.merriam-webster.com/dictionary/clamp].
Merriam-Webster, "Collimate," 2020 [online]; [Retrieved on Oct. 17, 2022], Retrieved from the Internet [URL: https://www.merriam-webster.com/dictionary/collimated].
Merriam-Webster, "Stream," n.d. [online]; [Retrieved on Dec. 13, 2018], Retrieved from the Internet [URL: https://www.merriam-webster.com/dictionary/stream].
Murube et al., "Classification of Artificial Tears, I: Composition and Properties", Advanced Experimental Medical Biology, 1998, vol. 438, pp. 693-704.
Murube et al., "Classification of Artificial Tears, II: Additives and Commercial Formulas", Advanced Experimental Medical Biology, 1998, vol. 438, pp. 705-715.
Oxford Online Dictionary, "Stream," n.d. [online]; [Retrieved on Dec. 13, 2018]; Retrieved from the Internet [URL: https://en.oxforddictionaries.com/definition/us/stream].
Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.
Vocabulary.com, "Stream," n.d. [online]; [Retrieved on Dec. 13, 2018]; Retrieved from the Internet [URL: https://www.dictionary.com/stream].

\* cited by examiner

MULTI-DOSE OCULAR FLUID DELIVERY SYSTEM

CROSS REFERENCE TO RELATED APPLICATIONS

This application claims the benefit of U.S. provisional patent application 62/814,773, filed on Mar. 6, 2019, and hereby incorporated by reference in its entirety.

FIELD OF THE INVENTION

This invention relates to delivery of liquids to the eye of a patient.

BACKGROUND

There are many instances where eye drops are employed in the treatment of ocular and other conditions. Depending on the condition being treated, eye drops may contain a variety of different active agents, including but not limited to: steroids, antihistamines, sympathomimetics, beta receptor blockers, parasympathomimetics, parasympatholytics, prostaglandins, nonsteroidal anti-inflammatory drugs (NSAIDs), antibiotics, antifungal, or topical anesthetics. Eye drops sometimes do not have medications in them and are only lubricating and tear-replacing solutions.

Generally, eye droppers are employed in the delivery of eye drops. Current eye drop devices often either require the head to be tilted back, the subject to lie down or provide downward traction on the lower eyelid, or a combination of traction and tilting, since the delivery mechanism typically relies on gravity for applying the medication. This is not only awkward, but involves a fair amount of coordination, flexibility and cooperation on the part of the subject to ensure that the medication gets into the eye while avoiding poking the eye with the dropper tip.

Current eye dropper bottles also pose the risk of poking the user in the eye, potentially causing physical damage to the eye, and further, exposing the tip to bacterial contamination due to contact with the eye. As such, the subject runs the risk of contaminating the medication in the eye drop bottle and subsequently infecting the eye.

A typical medical eye dropper dispenses single drops, typically of about 50 µL in volume. However, since the human eye can typically retain only 7 µL of fluid on the corneal surface, larger deposited volumes result in overflow and loss of most of the medication from the eye surface. In addition, a large volume of a single drop, such as 30 or 50 µL, causes a blinking reflex which removes a majority of the delivered fluid from the cornea as well as discomfort which leads to poor compliance. As a result, this method of administration is also inaccurate and wasteful. Moreover, the technology does not provide a satisfactory way of controlling the amount of medication that is dispensed, nor does it provide a way of ensuring that the medication that is dispensed actually lands on the eye and remains on the eye.

To date, most multi-dose containers for ophthalmic formulations generally include a preservative, which provides a number of functions, such as antimicrobial activity in the bottle and inhibition of decomposition of the active agent in the formulation. Examples of preservatives found in ophthalmic formulations include benzalkonium chloride (BAK), chlorobutanol, sodium perborate, and stabilized oxychloro complex (SOC). However, while providing benefits preservatives can also results in significant cytotoxic effects in the patient to whom the formulation is being administered.

As such, there continues to be a need for improved ophthalmic formulation delivery devices. The present inventors have discovered that of particular interest would be the development of a multi-dose delivery device that is capable of precisely administering to the eye small volumes of ophthalmic formulations, including preservative-free ophthalmic formulations.

SUMMARY

Multi-dose ocular fluid delivery devices are provided. Aspects of the fluid delivery devices include a fluid package and an actuator. The fluid package includes a reservoir of an ophthalmic formulation, an aperture and a valve member for sealing the aperture when fluid is not being ejected therethrough. The actuator is configured to operate the valve member so as to at least reduce, if not prevent, ingress of outside materials or contaminants into the reservoir, such that the ophthalmic formulation present in the reservoir does not require a preservative (e.g., where a preservative-free ophthalmic formulation is present in the reservoir). Also provided are methods of using the devices in fluid delivery applications, as well as a kit that includes components of the devices.

DETAILED DESCRIPTION

Multi-dose ocular fluid delivery devices are provided. Aspects of the fluid delivery devices include a fluid package and an actuator. The fluid package includes a reservoir of an ophthalmic formulation, an aperture and a valve member for sealing the aperture when fluid is not being ejected therethrough. The actuator is configured to eject the ophthalmic formulation through the aperture by providing a mechanical vibration to the vale member and/or to a wall of the reservoir.

This approach can at least reduce, if not prevent, ingress of outside materials or contaminants into the reservoir, such that the ophthalmic formulation present in the reservoir does not require a preservative (e.g., where a preservative-free ophthalmic formulation is present in the reservoir). Also provided are methods of using the devices in fluid delivery applications, as well as a kit that includes components of the devices.

In further describing various embodiments of the invention, the fluid delivery devices will be described first in greater detail, followed by a review of various methods of using the devices as well as kits that include the devices or components thereof.

Fluid Delivery Devices

As summarized above, aspects of the invention include multi-dose fluid delivery devices configured to eject an ophthalmic formulation, such as a preservative-free ophthalmic formulation, onto a target location of an eye of a subject, i.e., a target ocular location. The fluid delivery devices are, in some instances, configured to provide for self-administration of a fluid by a user to a target location of the user, e.g., a target ocular location. As such, the devices of such embodiments to allow the user to administer a volume of fluid to a target location of the user without any assistance from another individual, such as a health care practitioner.

While the nature of the fluid delivery devices may vary, in some instances the devices are handheld devices. By handheld device is meant that the device is dimensioned and has a weight such that it may be comfortably held by an average adult human hand. In some instances of handheld devices. By handheld device is meant that the device is dimensioned and has a weight such that it may be comfortably held by an average adult human hand. In some instances of handheld devices, the device has a longest dimension ranging from 10 to 500 mm, such as 20 to 250 mm, including 50 to 100 mm, such as 70 to 85 mm, and a weight ranging from 10 to 1000 g, such as 25 to 500 g, e.g., 40 to 100 g.

The fluid delivery devices described herein may include a fluid package having a reservoir and an aperture, an actuator component configured to eject fluid from the reservoir through the aperture and a valve member configured to seal the aperture when fluid is not being ejected therethrough. Additional components may also be present. Each of these components is now reviewed in greater detail.

Fluid Package

The fluid package component of devices of the invention is a fluid container that is configured to hold an amount of fluid and be operably coupled to an actuator, e.g., as described in greater detail below. The container may have any convenient configuration, and may be made of any convenient material, e.g., glass or plastic. The container may be configured to hold a single delivered dosage or multiple deliver delivered dosages, e.g., where the container comprises a volume of the liquid formulation sufficient to provide multiple delivered dosages, such that the reservoir is a multi-dose reservoir. As such, the volume of liquid formulation that the container is configured to hold may vary, ranging in some instances from 100 µl to 10 ml, such as 100 to 2000 µl, including 120 to 800 µl.

The container includes a reservoir component configured to hold an amount of a fluid, e.g., as described above, and one or more apertures through which fluid from the reservoir component may be ejected during use. While the number of apertures that a given fluid package has may vary, in some instances the number of apertures ranges from 1 to 20, such as 1 to 10, including 1 to 5, e.g., 1 to 4, 1 to 3, and 1 to 2. In some instances, the fluid package includes a single aperture. In some instances, the fluid package includes more than one aperture. The dimensions of a given aperture may vary, as desired. In some instances, the apertures have a longest dimension, e.g., diameter, ranging from 10 to 500µ, such as 50 to 450µ, e.g., 75 to 350µ, where in some instances the apertures have a diameter ranging from 80 to 120µ (such as 80 to 100µ), or 150 to 350 µ (such as 200 to 350µ, e.g., 250 to 300µ). Where desired, the aperture may include an antimicrobial material associated with at least a portion thereof, such as a portion or all of the internal surface of the aperture that is configured to mate with the valve member when in the sealed configuration. Examples of antimicrobial materials that may be present include, but are not limited to, antimicrobial metals, e.g., silver, copper, etc., antimicrobial coatings, e.g., parylene polymers, chlorhexidine and protamine sulfate compositions, and the like.

While the container may have any convenient configuration, in some instances the container includes an expanded, e.g., bulb, portion that includes the reservoir and a neck portion, e.g., that is configured to operably couple to an actuator and includes the one or more apertures. The fluid package is, in some instances, configured to be disposable.

As summarized above, the fluid package also includes a valve member configured to seal the aperture when fluid is not being ejected therethrough. As such, the valve member is configured to seal the aperture when fluid is not being ejected through the aperture, but not seal the aperture when fluid is being ejected through the aperture. The valve member is configured such to prevent ingress of outside materials or contaminants into the reservoir via the aperture when fluid is not being ejected through the aperture, allowing for the presences of the preservative-free ophthalmic formulation in the reservoir.

In some instances, the valve member includes a tip configured to mate with the aperture in a sealing relationship. The tip may have any convenient configuration. In some instances, the tip has a conical structure. In such instances, the conical tip may have a height ranging from 0.5 to 5.0 mm, such as 0.75 to 1.5 mm and a bottom diameter ranging from 0.4 to 4.0 mm, such as 1.5 to 2.5 mm. In other embodiments, the tip may be a rounded sealing structure, which in some instances may have a half-spherical structure, with a bottom diameter ranging from 0.4 to 4.0 mm, such as 1.5 to 2.5 mm.

In some instances, the fluid package may include a vent, e.g., to provide for introduction of gas into the reservoir as fluid is ejected from the fluid package and provide for consistent fluid ejection. The vent may be configured to provide entry of microbial free air into the reservoir from outside of the package. Any convenient vent configuration may be employed. An example of such a vent includes a lumen that extends from an opening in the neck region to a location in the reservoir, such as near the end of the fluid package furthest from the neck region. The dimensions of the lumen may vary, where in some instances the lumen has a length ranging from 5.0 to 20 mm, such as 12 to 18 mm and an inner diameter ranging from 0.5 to 2.0 mm, such as 0.7 to 1.0 mm. The opening of the lumen in the neck region may be covered, e.g., to prevent ingress from microbial, e.g., bacteria, and other undesired agents into the fluid package. In such instances, the covering may have antimicrobial properties, e.g., where covering is a porous membrane having a pore size configured to prevent passage of microbes, e.g., bacteria, such as pore sizes of 0.22 µm or less, such as 0.2 µm or less, e.g., 0.15 µm or less. Alternatively or in addition, the cover may include one or more antimicrobial agents, including but not limited to, antimicrobial metals, e.g., silver, copper, etc., antimicrobial coatings, e.g., parylene polymers, chlorhexidine and protamin sulfate compositions, and the like.

In some instances, the expanded region of the fluid package is separable from the neck region, e.g., where the two components are not fabricated as single, integrated structure. In such instances, the expanded region may be a standard ophthalmic bottle. In such instances, the length of the standard ophthalmic bottle may range from 25 to 45 mm, such as 30 to 35 mm. The inner diameter of the standard ophthalmic bottle may range from 5.0 to 30 mm, such as 13 to 20.0 mm. The internal volume of the standard ophthalmic bottle may range from 2.0 to 14.0 ml, such as 2.0 to 5.0 ml. The diameter of the opening of the standard ophthalmic bottle may vary, ranging from 4.0 to 13.0 mm, such as 8.0 to 11.0 mm. The bottle may be fabricated from any convenient material, including glass and polymeric materials.

In such instances, the neck region may be mated to the standard ophthalmic bottle, where the neck region includes the aperture, valve member and vent, e.g., as described above. The neck region may be mated to the bottle using any convenient configuration, e.g., press-fit, screw on, etc.

Actuator

In addition to the fluid package, the device further includes an actuator component configured to operably couple to the fluid package and eject fluid from the reservoir of the fluid package through the one or more apertures to the target location. In some instances, the actuator is a component that is configured to impart vibration to the contents of the container, where the oscillation frequency of the vibration may vary. In some instances, the frequency is in the audible range, such as from 20 to 20000 Hz, e.g., 50 to 10000 Hz, including 500 to 1000 Hz. In some instances, the oscillation frequency is an ultrasonic frequency, ranging in some instances from 10 to 1000 KHz, such as 20 to 800 KHz, and including 20 to 35 KHz.

In some instances, the actuator is configured to produce pressure fluctuations in the fluid inside of the fluid package so as to eject fluid from the reservoir through the aperture. In some instances, the actuator produces pressure fluctuations in the fluid by displacement induced on an external surface of the fluid package. The oscillations, e.g., of audible or ultrasonic frequency (such as described above) imparted by the actuator on the fluid package, and in some instances the outer surface of the fluid package, produces cycles of acoustic pressure in the fluid held by the fluid package, resulting in ejection of fluid from the one or more apertures. In some instances, the fluid is ejected from the fluid package by the actuator as a stream, where the stream may be a continuous stream of liquid (i.e., a stream that is not made up of individual droplets) or a discontinuous stream of liquid, e.g., a collimated stream of individual droplets. A discontinuous fluid stream can also be a succession of elongated fluid blobs separated by relatively short intervals. Also, it is possible for the configuration of the stream to vary as the distance between the ejected fluid and the aperture increases. Where the stream is a continuous stream of liquid, the stream diameter may vary, and in some instances ranges from 0.05 to 0.3 mm, such as from 0.05 to 0.2 mm, including 0.05 to 0.15 mm, such as 0.070 to 0.130 mm. Where the stream is a discontinuous stream of individual droplets, the volume of the individual droplets may vary, ranging in some instances from 50 to 1500 µl, such as 100 to 1000 µl. In some instances, the width of the stream, which may be continuous, discontinuous, or have a component that is continuous and a component that is discontinuous, may by substantially constant along the length of the stream, such that any variation in the width of the stream from the one or more apertures to the target location varies by 5% or less, such as 2% or less. The duration of stream delivery during a given administration event may vary and is selected so as to provide the desired delivered dosage volume. In some instances, the duration of stream delivery, i.e., the duration of administration, ranges from 10 to 3000 msec, such as 100 to 2000 msec, such as 250 to 1000 msec, including 400 to 600 msec. Other feasable dose durations are durations of 300 ms or less, and more preferably 150 ms or less.

While the nature of the actuator component may vary, in some instances the actuator component is an electromagnetic actuator. In such embodiments, an electromagnetic actuator imparts an oscillation amplitude at low frequency, which in some instances is within the audible range (e.g., 20 to 20,000 Hz). In some instances, the electromagnetic actuator operates in the audio range of frequencies, but produces low audible tone, generally 30 dB or lower. At the same time, the device emits fluid from a sufficiently large nozzle at sufficiently low velocity to minimize the discomfort associated with topical delivery to the eye.

Illustrative Embodiments

Figure 1:
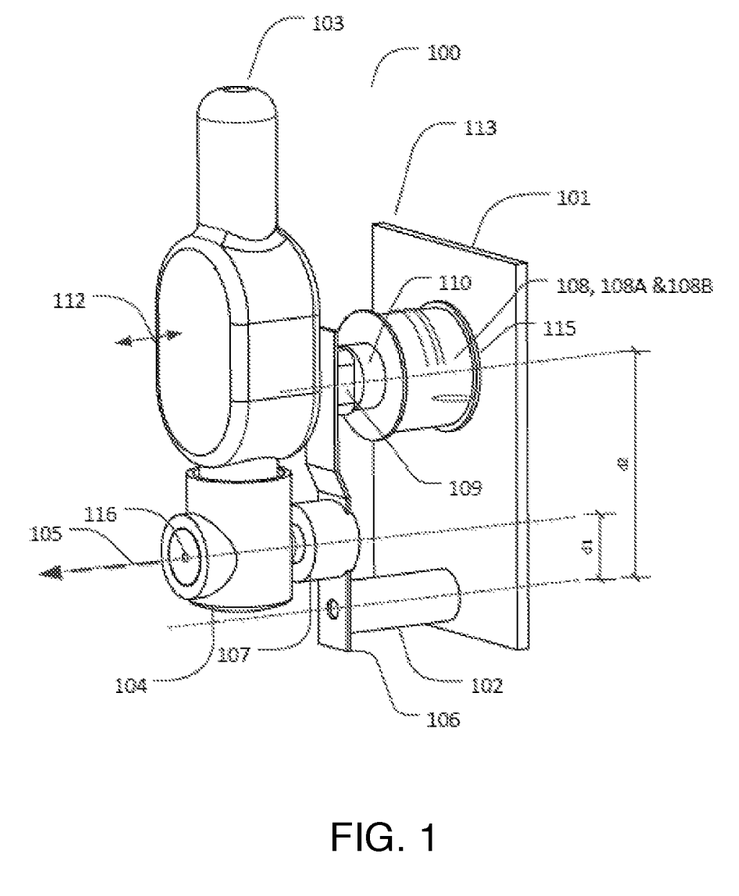
FIG. 1 illustrates a perspective view of an embodiment of the invention.
Figure 2:
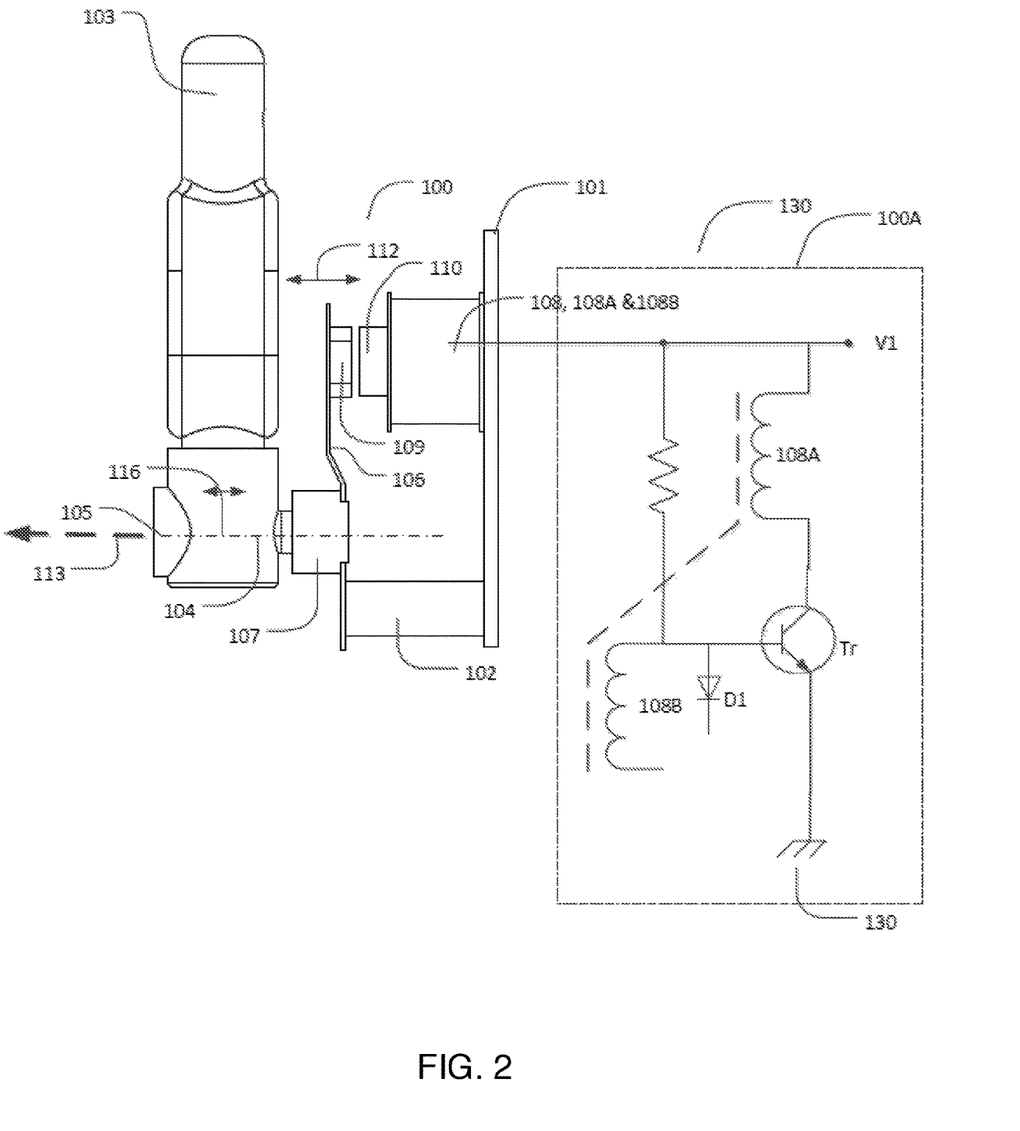
FIG. 2 illustrates a side view of the example of FIG. 1, as well as the electronic circuit thereof.
Figure 3:
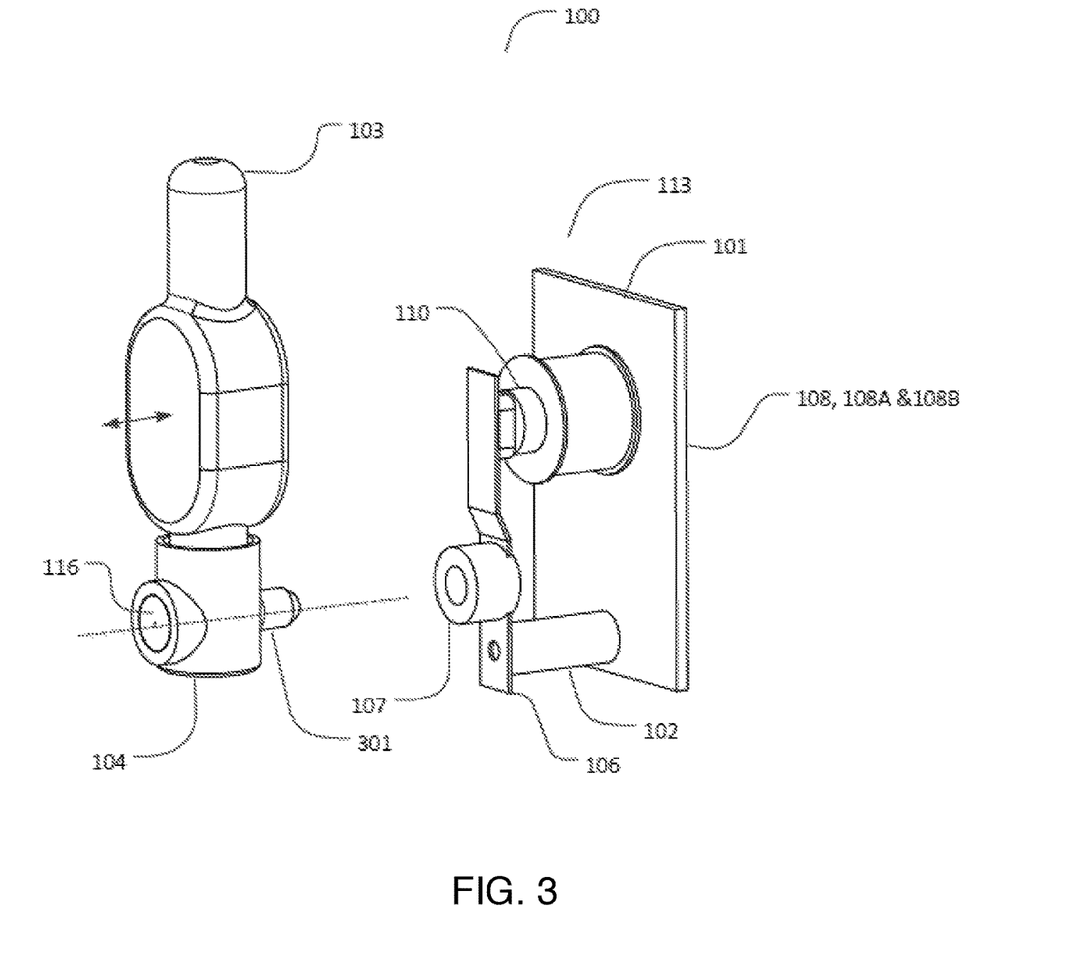
FIG. 3 illustrates an exploded view of the example of FIG. 1 and FIG. 2 showing the ampule and the magnetic transducer separately.

An embodiment of the invention is illustrated in FIGS. 1-3. Referring to FIG. 1, which illustrates the electromagnetic dispensing device (100) of the present invention. Device (100) includes an ampoule (103) containing a fluid to be dispensed and further includes an electromagnetic transducer (113) that is configured to oscillate the ampoule such that the fluid is dispensed through aperture (116) at the lower part of the ampoule.

Transducer (113) comprises a base plate (101), electromagnet (115) and a permanent magnet (109). Electromagnet (115) comprises a ferromagnetic core pin (110) and a coil (108) that is wound around the core pin. Permanent magnet (109) is positioned in a close proximity to the electromagnet core pin (110) and is suspended by a flexible cantilever beam (106). Alternating magnetic field generated by coil (108) produces magnetic force and mechanical oscillations of permanent magnet (109) and the flexible cantilever beam (106) that supports it. Cantilever beam includes an anchor (107) which supports and transmits the oscillation of the cantilever beam to the ampoule. The device further includes a standoff support pin (102) that extends from the base plate (101) and provides a support to the cantilever beam (106).

In the illustrated embodiment, permanent magnet (109) is positioned at the free end of cantilever beam at a distance of (d2) from the cantilever beam support (102) while the ampoule support anchor (107) is at a distance of (d1) from the beam support (102). In this way a mechanical advantage is obtained, and the force applied to the ampule is amplified by the ratio of the distances d2/d1 relative to the force applied to the permanent magnet. In the illustrated embodiment the ampoule contains 1 mL of aqueous solution and has a mass of approx. 1 gm. Accordingly, the force that is required to oscillate the ampoule at an amplitude of approximately 20-60 mm is about 0.2N to 1N. In the illustrated embodiment, the distance d2 is 13.5 mm and distance d1 is 1.35 mm. The ratio d2/d1 is about 10, and the oscillation amplitude is between 20 µm to 60 µm, depending on the input voltage. In the illustrated embodiment, the diameter of the dispensing aperture ranges between 200 and 350 and such a large aperture dispenses only at high oscillation amplitude.

In the illustrated embodiment the ferromagnetic core (110), base plate (101) and support pin (102) are made of a soft magnetic material, such as 4750 alloy, or other alloys that have low corrective force and minimal magnetic hysteresis can be used.

Ampoule (103) is oriented such that the dispensing nozzle (116) is aligned with the oscillation amplitude of the cantilever beam (106). The oscillations generate pressure fluctuation inside the ampoule and fluid is ejected from nozzle (116) as illustrated by the arrow (105)

Permanent magnet (109) may be made of a rare-earth magnetic material, such as Neodymium N35, N38, N42, Samarium Cobalt or the like. Non-rare-earth alloy such as iron, nickel and cobalt may also be used.

Referring now to FIG. 2, this figure shows magnetic transducer (100) and further includes a diagram of the electrical circuit that generates alternating electrical signal from a DC source, such as a battery cell.

Electromagnetic transducer (100) includes a circuit (100A) which produces alternating current which is fed to the coil (108) to generate a magnetic force which oscillates permanent magnet (109). Coil (108) defines two separate magnetic coils, the first is primary coil (108A) and the second is detection coil (108B). Both coils (108A) and (108B) are wound around the iron core (110). When DC voltage is connected to the primary coil (108A) current flows and the electromagnetic force that is developed pulls permanent magnet (109) toward core (110). At the same time the current in the primary coil (108A) produces transient, time-dependent electromagnetic induction, which induces electromotive force (EMF) and electrical current in the detection coil (108B), the current is fed to a bipolar transistor (Tr) which switches off the current from the primary coil (108A) by pulling it to the ground (130). As a result, magnetic force returns to zero and magnet (109) return to its normal position. Subsequently, primary coil (108A) turns on again and pulls back the magnet. In this way the alternating magnetic field is generated using a DC input voltage from a DC battery. In this example, transistor (Tr) is an NPN general purpose amplifier, such as Fairchild model 2N3904. The circuit further includes a Zener diode (D1) that regulates the voltage. Magnetic coil (108A) and (108B) have an inductance that ranges from 1-10 mH and are configured to generate a magnetic field to oscillate the magnet (109). Generally, the mass of magnet (109) is small to reduce the inertial load and increase the oscillation amplitude. In one embodiment, the mass of permanent magnet (109) is 0.075 gm. Beam (106) is made of stainless steel alloy 304 having a thickness of 0.2 mm, a width of 5 mm and a free length of 13.5 mm. In the illustrated embodiment, the beam has a natural frequency of about 523 Hz while the driving frequency of magnetic oscillator is about 1100 Hz.

FIG. 3 illustrates an exploded prospective view of the dispensing device (100), showing the ampoule (103) and the electromagnetic transducer (113) separately. It can be seen that ampule (103) includes a pin member (301) that is inserted into anchor member (107) in a tight interference fit. In this way the oscillations that are generated by the transducer are transmitted to the ampoule.

Figure 4:
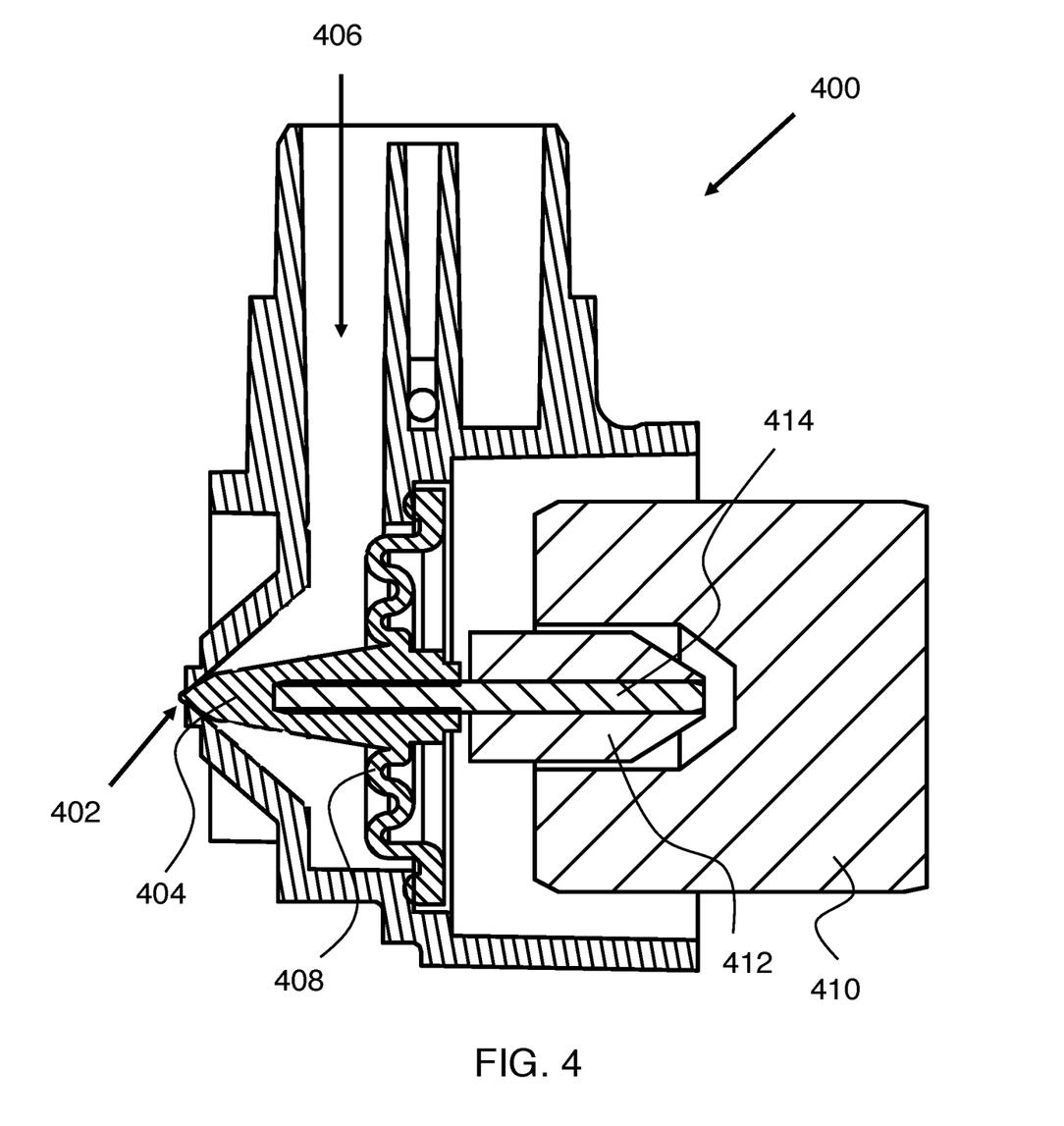
FIG. 4 is an enlarged cross section view of an aperture configuration suitable for use in embodiments of the invention.
Figure 5A:
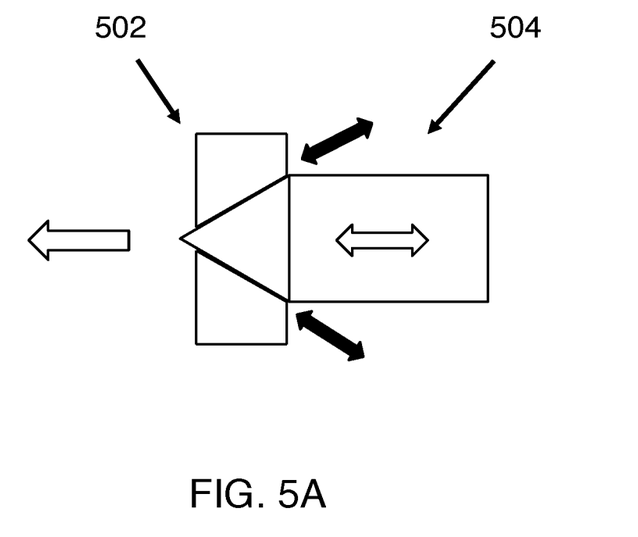
FIGS. 5A-B schematically show operating principles of the aperture configuration of FIG. 4.
Figure 5B:
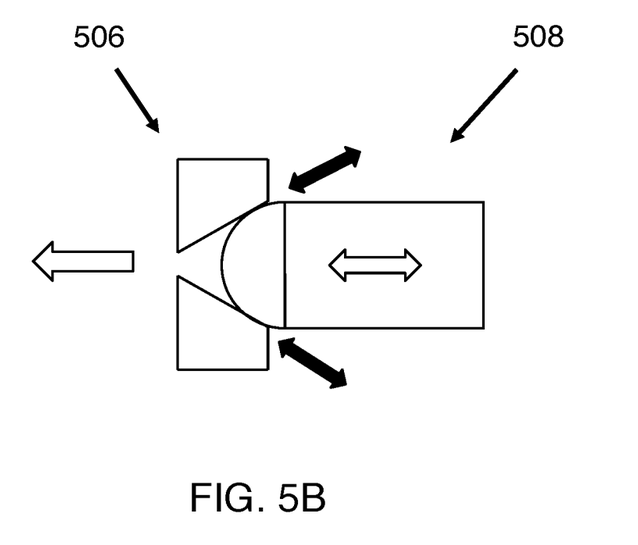

In the views of FIGS. 1-3, the scale is such that the valve member that seals the aperture when fluid is not being dispensed is too small to be shown. Accordingly, FIG. 4 is an enlarged cross section view of a fluid dispenser (400) operating according to the above described principles and showing the valve member. The example of FIG. 4 has the same principles of operation as described above, but differs in some details of its configuration.

Here (402) is the aperture, (404) is the valve member, liquid being dispensed is present in reservoir (406) (only partially shown here), (408) is a flexible diaphragm to which valve member (404) is affixed, (410) is a solenoid for the electromagnetic actuator, and (412) is a metal cylinder with a conical end. Metal cylinder (412) is composed of a magnetic ferrous alloy so that it can be attracted by the magnetic flux generated by solenoid (410). Member (414) connects (412) to valve member (404)/diaphragm (408). The combination of solenoid (410) and (412) provides an electromagnetic actuator having operating principles as described above. From FIG. 4 it is apparent that the resulting motions in the fluid dispenser from this actuator are vibration of valve member (404) into and out of engagement with aperture (402), and a vibration of diaphragm (408). More generally, this can be regarded as a mechanical vibration of the valve member and/or a mechanical vibration of part of the wall of the reservoir. As described generally above, the valve member and/or aperture may include an antimicrobial material.

Diaphragm (408) holds valve member (404) in engagement with aperture (402) such that aperture (402) is sealed except when fluid is being ejected. In detailed designs, the mechanical stiffness of diaphragm (408) can be selected to provide an appropriate degree of mechanical force for this engagement.

Fluid can be ejected by vibrating valve member (404) and/or by setting up pressure fluctuations in the fluid sufficient to overcome the seal. As in this example, both physical effects can result from a single vibrating actuator. FIGS. 5A-B schematically show these two physical effects. In the example of FIG. 5A, a first process for fluid ejection from aperture (502) (left-facing block arrow) results from vibrating the tip of valve member (504) into and out of engagement with aperture (502). This vibration of the valve member is schematically shown with an open double headed block arrow. A second process for fluid ejection from aperture (502) is due to forces exerted as a result of pressure fluctuations in the fluid that are sufficient to eject the fluid past the valve member. Forces resulting from these pressure fluctuations in the fluid are schematically shown with solid black double headed block arrows. In the example of FIG. 4, such pressure fluctuations can be due to vibration of diaphragm (408) and/or motion of valve member (404). The example of FIG. 5B is similar, except that valve member (508) has a rounded tip as described above that engages with aperture (506) to seal the aperture except when fluid is being dispensed. It is expected that valve member vibration and fluid pressure fluctuations can contribute to fluid ejection individually or in any combination.

Methods

As summarized above, aspects of the present disclosure include methods of administering an active agent to a target location, such as an ocular location, of a subject. By target ocular location is meant a region (i.e., area or domain) of an eye surface, such a region of a cornea, a region of a conjunctiva, a region that includes both corneal and conjunctival components, etc. In some instances, the target ocular location is an area or region that is offset relative to the optical axis of the eye. In some instances, the target location is on either the bulbar or tarsal conjunctiva, or in the conjunctival fornix. In other words, the target topical ocular location is one that is displaced from the center of the pupil or the center of the iris. While the magnitude of the distance of the offset/displacement may vary, in some instances the magnitude ranges from 1 to 20 mm, such as 2 to 20 mm, e.g., 5 to 15 mm, including 5 to 10 mm. While the target topical ocular location may vary in size, in some instances the size of the target topical ocular region is 15 $mm^2$ or less, ranging in some instances from 1 to 15 $mm^2$, such as from 2.5 to 12 $mm^2$, including from 3 to 9 $mm^2$.

Aspects of embodiments of the methods include delivering to the target location a dosage of a liquid formulation of the active agent. In some instances, the delivered dosage is a dosage having a volume that can be wholly accommodated by the tear film of the target topical ocular location. The tear film of the target topical ocular location is the film that is associated with the target topical ocular location. As such, the tear film is the film or layer of tear liquid that is present on the eye surface on which the target topical ocular location, e.g., as described above, is located. As the delivered dosage has a volume that may be wholly accommodated by the tear film of the target topical ocular location, it may also be a volume that may be wholly accommodated by the ocular surface that includes the target topical ocular location. By "wholly accommodated by the ocular surface" is meant that, upon delivery, the delivered dosage has a volume that can be held on the surface of the eye to which it is administered without any excess liquid running off of the surface of the eye and over the eyelid, e.g., in the form of tears. While the volume of a given delivered dosage may vary, in some instances the volume ranges from 1 to 15 µl, such as 5 to 10 µl.

In some instances, the delivered dosage is one that has an efficacy comparable to a reference dosage having a volume that exceeds the capacity of the tear film of the target topical ocular location. The reference dosage in such instances, apart from volume, is otherwise identical to that of the delivered dosage. As such, the concentration of the active agent in the reference dosage is the same as the concentration of the active agent in the delivered dosage. The volume of the reference dosage exceeds that of the delivered dosage, e.g., by 2 fold or greater, such as 3 fold or greater. In some instances, the reference dosage has a volume ranging from 25 to 60 µl, such as 30 to 50 µl. In some instances, the reference dosage is a dosage that is delivered by a standard eye dropper device.

The delivered dosage of the liquid formulation of the active agent may be administered to the target topical ocular location as a stream, where the stream may be a continuous stream of liquid (i.e., a stream that is not made up of individual droplets) or a discontinuous stream of liquid, e.g., a collimated stream of individual droplets, or include both continuous and discontinuous components. Where the stream is a continuous stream of liquid, the stream diameter may vary, and in some instances ranges from 0.05 to 0.15 mm, such as 0.070 to 0.130 mm. Where the stream is a discontinuous stream of individual droplets, the volume of the individual droplets may vary, ranging in some instances from 50 to 1500 µl, such as 100 to 1000 µl. The velocity of the stream may vary, ranging in some instances from a value generally above the minimum exit velocity of the fluid from the aperture. The minimum exit velocity is defined in a scientific article titled "Production of uniform-size liquid droplets" N. R. Lindblad and J. M Scheider equation 2. This article is incorporated herein by reference. In some instances, the exit velocity is 20% or more above the minimum exit velocity and in some instances is 300% or less above the minimum exit velocity. For example, for an aperture size of 125 micron the minimum velocity is 194 cm/sec but the selected velocity would at least 30% higher i.e., 252 cm/sec. The duration of stream delivery during a given administration event may vary and is selected so as to provide the desired delivered dosage volume, e.g., as described above. Ideally, duration of stream delivery should be below the blink response time, i.e., below 150 ms. If necessary, the duration of administration could be extended for 250 ms or even up to 1000 msec. In some instances, the duration is 100 ms or longer.

The delivered dosage may be administered to the target topical ocular location using any convenient protocol. In some instances, the delivered dosage is administered to the target topical ocular location by an individual other than the subject, e.g., where the delivered dosage is administered by a health care professional, such as a physician or nurse. In other instances, the delivered dosage is self-administered by the subject, e.g., where the subject administers the dosage to a target topical ocular location of one of the subject's own eyes.

The fluid present in the fluid package may vary, as desired. In some instances, the fluid present in the fluid delivery package is a liquid formulation of an active agent. The terms "agent," "compound," and "drug" are used interchangeably herein to refer to a molecule or molecular combination that has a physiological effect upon contact with a subject via administration to the target topical location of the subject. Examples of active agents that may present in the liquid formulation include, but are not limited to: anti-infectives (including but not limited to antibiotics, antivirals, etc.), anti-inflammatories (including but not limited to steroids and non-steroidal anti-inflammatory drugs (NSAIDS), etc.), anti-allergy agents (including but not limited to anti-histamines and mast cell stabilizers, etc.), anti-fungals, cholinergic agents, anti-cholinergic agents including both long acting and short acting agents (e.g., atropine, tropicamide, etc.), vasoconstrictors, biologics (e.g. proteins, engineered proteins, etc.), small molecules, anesthetics, analgesics, intraocular pressure lowering agents (including but not limited to prostaglandin analogs, ROK inhibitors, beta blockers, carbonic anhydrase inhibitors, and alpha agonists, etc.), lubricants (including but not limited to saline, polymer solutions, proteoglycans, glycosaminoglycans, carbohydrates, etc.), mydriatic (pupil dilating) agents, miotic agents (pupil constricting agents), iodine derivatives, etc.; and/or various combinations thereof. The concentration of the cholinergic agent in a given liquid formulation of a micro-dose may vary. In some embodiments, the concentration of cholinergic agent in the liquid formulation of the micro-dose ranges from 50 ng/ml to 100 mg/ml.

In addition to the active agent, the liquid formulation may include an aqueous delivery vehicle, e.g., a pharmaceutically acceptable aqueous vehicle. In addition to water the aqueous delivery vehicle may include one or more additional components, including but not limited to: salts, buffers, preservatives, solubility enhancers, viscosity modulators, colorants, etc. Suitable aqueous vehicles include sterile distilled or purified water, isotonic solutions such as isotonic sodium chloride or boric acid solutions, phosphate buffered saline (PBS), propylene glycol and butylene glycol. Other suitable vehicular constituents include phenylmercuric nitrate, sodium sulfate, sodium sulfite, sodium phosphate and monosodium phosphate. Additional examples of other suitable vehicle ingredients include alcohols, fats and oils, polymers, surfactants, fatty acids, silicone oils, humectants, moisturizers, viscosity modifiers, emulsifiers and stabilizers. The compositions may also contain auxiliary substances, e.g., pH adjusting agents such as sodium hydroxide, hydrochloric acid or sulfuric acid; and viscosity increasing agents such as methylcellulose.

As summarized above, ophthalmic formulations present in the reservoir may be preservative-free. By "preservative-free" is meant that the formulations do not include any preservative agents, such as but not limited to, antimicrobial agents such as benzalkonium chloride (BAK), chlorobutanol, sodium perborate, and stabilized oxychloro complex (SOC), parabans and organic mercurial compounds.

An exemplary final composition is sterile, preservative-free, essentially free of foreign particles, and has a pH that allows for patient comfort and acceptability balanced with a pH that is desirable for optimum drug stability. An exemplary "pharmaceutically acceptable vehicle" is an "ophthalmically acceptable vehicle" as used herein refers to any substance or combination of substances which are non-reactive with the compounds and suitable for administration to patient. In an exemplary embodiment, the vehicle is an aqueous vehicle suitable for topical application to the patient's eyes. In various embodiments, the vehicle further includes other ingredients which may be desirable to use in the ophthalmic compositions of the present invention include antimicrobials, preservatives, co-solvents, surfactants and viscosity building agents.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

In some aspects of the subject methods, the method further comprises the step of measuring efficacy of a given condition, e.g., of a disease condition in the subject. In some such instances, the determination is made by comparing the results to the results performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more. The evaluation may vary depending on the nature of the condition being treated. In some embodiments, the subject methods further include diagnosing an individual as having a given condition.

The above methods find use in a variety of different applications. Certain applications are reviewed in greater detail in the Utility section, below.

Utility

The subject devices and methods find use in a variety of different applications, including both treatment and diagnostic/examination applications. The term "treating" or "treatment" as used herein means the treating or treatment of a disease or medical condition in a subject or patient, such as a mammal (such as a human), where the term includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

An example of a condition that may be treated using methods/devices of the invention is glaucoma. Glaucoma is a collection of disorders characterized by progressive visual field loss due to optic nerve damage. It is the leading cause of blindness in the United States, affecting 1-2% of individuals aged 60 and over. Although there are many risk factors associated with the development of glaucoma (age, race, myopia, family history, and injury), elevated intraocular pressure, also known as ocular hypertension, is the only risk factor successfully manipulated and correlated with the reduction of glaucomatous optic neuropathy. In glaucoma associated with an elevation in eye pressure the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The aqueous or aqueous humor is a transparent liquid that fills the region between the cornea at the front of the eye and the lens. The aqueous humor is constantly secreted by the ciliary body around the lens, so there is a continuous flow of the aqueous humor from the ciliary body to the eye's front chamber. The eye's pressure is determined by a balance between the production of aqueous and its exit through the trabecular meshwork (major route) or via uveal scleral outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanilicular meshwork).

In embodiments where the methods and devices are used in treating glaucoma, the delivered dosage may include an intraocular pressure modulatory agent. An "intraocular pressure modulatory agent" can comprise a drug and may be any of the following or their equivalents, derivatives or analogs, including anti-glaucoma medications (e.g. adrenergic agonists, adrenergic antagonists (beta blockers), carbonic anhydrase inhibitors (CAIs, systemic and topical), therapeutic agent(s) such as prostaglandins, prostaglandin precursors, including antiglaucoma drugs including beta-blockers such as timolol, betaxolol, levobunolol, atenolol (e.g., as described in U.S. Pat. No. 4,952,581); adrenergic agonists including clonidine derivatives, such as apraclonidine or brimonidine (e.g., as described in U.S. Pat. No. 5,811,443); and prostaglandin analogues such as bimatoprost, travoprost, tafluprost, latanoprost, etc. In some instances, the therapeutic agent is already marketed for glaucoma, and commercially available preparations thereof can be used. Further therapeutic agents include carbonic anhydrase inhibitors such as acetazolamide, dorzolamide, brinzolamide, methazolamide, dichlorphenamide, diamox; and the like.

Diagnostic/examination applications include, but are not limited to, mydriasis applications where the pupil is dilated, e.g., to permit examination of the retina and other deep structures of the eye. Mydriatic agents that may be employed in such applications include, but are not limited to: atropine, atropine sulfate, atropine hydrochloride, atropine methylbromide, atropine methylnitrate, atropine hyperduric, atropine N-oxide, phenylephrine, phenylephrine hydrochloride, hydroxyamphetamine, hydroxyamphetamine hydrobromide, hydroxyamphetamine hydrochloride, hydroxyamphetamine iodide, cyclopentolate, cyclopentolate hydrochloride, homatropine, homatropine hydrobromide, homatropine hydrochloride, homatropine methylbromide, scopolamine, scopolamine hydrobromide, scopolamine hydrochloride, scopolamine methylbromide, scopolamine methylnitrate, scopolamine N-oxide, tropicamide, tropicamide hydrobromide, and tropicamide hydrochloride.

Kits

Also provided are kits that find use in practicing embodiments of the methods, such as those described as described above. The term "kit" refers to a packaged delivery device or component thereof, e.g., ampule, such as described above. In addition to the above-mentioned components, kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The invention claimed is:

1. An apparatus for deliver a fluid to an eye of a patient, the apparatus comprising:
   a fluid package comprising a reservoir configured to hold a fluid, an aperture, and a valve member configured to seal the aperture when fluid is not being ejected through the aperture;
   an actuator configured to eject the fluid through the aperture by providing a mechanical vibration to the valve member and/or to a wall of the reservoir;
   wherein the fluid package comprises a resilient diaphragm configured to hold a tip of the valve member in engagement with the aperture when fluid is not being ejected through the aperture;
   wherein the valve member is affixed to the resilient diaphragm;
   wherein the actuator provides the mechanical vibration by driving motion of a connecting member connecting the actuator to the valve member.

2. The apparatus of claim 1, wherein the actuator is configured to eject the fluid from the aperture by vibrating a tip of the valve member into and out of engagement with the aperture.

3. The apparatus of claim 1, wherein the actuator is configured to generate pressure fluctuations in the fluid sufficient to eject the fluid through the aperture and past the valve member.

4. The apparatus of claim 1, wherein the fluid is a preservative-free ophthalmic solution.

5. The apparatus of claim 1, wherein the reservoir is a multi-dose reservoir.

6. The apparatus of claim 1, wherein the valve member has a conical tip that engages with the aperture.

7. The apparatus of claim 1, wherein the valve member has a rounded tip that engages with the aperture.

8. The apparatus of claim 1, wherein the valve member has a tip that engages with the aperture, and wherein the tip comprises an anti-microbial material.

9. The apparatus of claim 1, wherein the aperture comprises an anti-microbial material.

10. The apparatus of claim 1, wherein the actuator comprises an electromagnetic transducer disposed on an external surface of the reservoir and configured to induce vibration of at least part of a wall of the reservoir.

11. The apparatus of claim 10, wherein the actuator is configured to eject fluid from the aperture by generating pressure fluctuations in the fluid due to the vibration.

12. The apparatus of claim 1, wherein the apparatus is configured to deliver a dose volume of 1 to 15 µl.

13. The apparatus of claim 1, wherein the apparatus is configured to deliver a dose in 150 ms or less.

* * * * *